United States Patent [19]
Stein

[11] Patent Number: 5,132,995
[45] Date of Patent: Jul. 21, 1992

[54] X-RAY ANALYSIS APPARATUS

[75] Inventor: Jay A. Stein, Framingham, Mass.

[73] Assignee: Hologic, Inc., Waltham, Mass.

[21] Appl. No.: 564,156

[22] Filed: Aug. 7, 1990

Related U.S. Application Data

[63] Continuation-in-part of Ser. No. 319,994, Mar. 7, 1989, Pat. No. 5,040,199, which is a continuation-in-part of Ser. No. 78,419, Jul. 27, 1987, Pat. No. 4,811,373, which is a continuation-in-part of Ser. No. 885,098, Jul. 14, 1986, Pat. No. 4,947,414.

[51] Int. Cl.$^5$ ............................................. G01N 23/06
[52] U.S. Cl. ........................................ 378/56; 378/55; 378/146
[58] Field of Search ............................ 378/51–56, 378/145, 146, 147, 155, 62, 19, 11, 4, 196

[56] References Cited

U.S. PATENT DOCUMENTS

| Re. 28,544 | 9/1975 | Stein et al. | 250/369 |
|---|---|---|---|
| 4,029,963 | 6/1977 | Alvarez et al. | 378/62 |
| 4,160,167 | 7/1979 | Weiss et al. | 250/445 T |
| 4,206,363 | 5/1980 | Hounsfield et al. | 250/445 |
| 4,282,510 | 8/1981 | Southgate | 340/146.3 |
| 4,383,327 | 5/1983 | Kruger | 378/19 |
| 4,426,721 | 1/1984 | Wang | 378/99 |
| 4,639,941 | 1/1987 | Hounsfield | 378/11 |
| 4,644,578 | 2/1987 | Paolini | 378/146 |
| 4,707,786 | 11/1987 | Dehner | 364/414 |
| 4,736,401 | 4/1988 | Donges et al. | 378/146 |
| 4,811,373 | 3/1989 | Stein | 378/56 |
| 4,817,119 | 3/1989 | Ledley et al. | 378/9 |
| 4,817,123 | 3/1989 | Sones et al. | 378/98 |
| 4,947,414 | 8/1990 | Stein | 378/56 |
| 5,040,199 | 8/1991 | Stein | 378/56 |

OTHER PUBLICATIONS

Rutt et al., "High-Speed, High-Precision Dual Photon Absorptiometry", (the University of California at San Francisco), a poster exhibited at a meeting of the American Society for Bone and Mineral Research held on Jun. 16, 1985 in Washington, D.C., 5 to 10 copied of which were provided within 2 weeks to people at their request.

Stein, "X-Ray Imaging with a Scanning Beam", Radiology, vol. 117, No. 3, pp. 713–716, Dec. 1975.

Gustafsson et al., "X-Ray spectrophotometry for bone-mineral determinations", Medical and Biological Engineering, Jan. 1974, pp. 113–118.

Primary Examiner—David P. Porta
Attorney, Agent, or Firm—Fish & Richardson

[57] ABSTRACT

X-ray analysis apparatus and related method including a bone densitometer apparatus, in which detectors are translatable in the plane of the fan beam for each scan line position to provide enhanced signal-to-noise ratio and resolution, and detector-to-detector normalization. In this motion, the detectors move relative to an x-ray source and an object or patient. Indexing or moving from one scan line position to the next involves relative movement between the object or patient, and the x-ray source and detectors, which are fixed in relationship to each other during this indexing.

26 Claims, 7 Drawing Sheets

FIG. 1b  FIG. 1a

X-RAY ANALYSIS APPARATUS

BACKGROUND OF THE INVENTION

This application is a continuation-in-part of and incorporates by reference U.S. Ser. No. 07/319,994 filed Mar. 7, 1989, now issued as U.S. Pat. No. 5,040,199, which in turn is a continuation-in-part of U.S. Ser. No. 07/078,419 filed Jul. 27, 1987, now issued as U.S. Pat. No. 4,811,373, which in turn is a continuation-in-part of U.S. Ser. No. 06/885,098 filed Jul. 14, 1986, now issued as U.S. Pat. No. 4,947,414.

This invention relates to x-ray analysis apparatus.

In one important type of x-ray analysis apparatus, radiation is used to measure the density and distribution of bone in the human body. This procedure is helpful in diagnosing bone disease such as osteoporosis. Since this diagnostic technique uses potentially harmful ionizing radiation, bone densitometers are typically constructed to minimize the radiation exposure by minimizing the duration of radiation exposure while at the same time using the lowest intensity of the radiation possible.

In general, in a bone densitometer, a patient is placed on a table while a radiation source passes radiation through the patient. A detector is positioned on the opposite side of the patient from the source to detect the unattenuated radiation. Both x-ray tubes and radioisotopes have been used as a source of x-ray radiation. In each case, the radiation from the source is collimated to a specific beam shape prior to reaching the patient. This collimation reduces the exposure of the patient to the predetermined region of the patient opposite which are located the detectors. Various x-ray beam shapes have been used in practice and include fan beam, pencil beam, and cone beam shapes.

The shape of the beam and the shape of the detector system correspond. The detector in a fan beam system is a linear array of detectors. The actual detectors which make up the array range from low cost silicon photodiodes coupled with a scintillation material for use with higher intensity radiation to higher cost photomultiplier tubes coupled with scintillation material for use with low intensity radiation.

Since in bone densitometry the intent is to reduce the radiation exposure to the patient and since only a small percentage of x-ray penetrate the patient, highly sensitive photomultiplier tubes with scintillation are useful. Such photomultiplier detectors are expensive, those of lowest cost being relatively large and therefore of relatively low inherent resolution.

SUMMARY OF THE INVENTION

According to an important aspect of the invention, an x-ray analysis apparatus comprises an x-ray means which generates and projects at least one x-ray beam in a plane transverse to an object, and detector array means arranged on the opposite side of the object to detect x-rays to produce signals corresponding to the amount of x-rays transmitted through the object. The detector array means together with and in fixed relation to the x-ray means is movable relative to the object in a scanning direction normal to the beam through a multiplicity of scan line positions. Furthermore, the detector array means at each scan position of the x-ray means is movably driven relative to the x-ray means and the patient or other object in a second direction in the plane of the beam and transverse to the object, means being provided to produce multiple samples of the signal of the detector array means at each scan position of the x-ray means during the movement of the detector array means in the second direction. Signal processing means responsive to signals thus produced from the detector array means produces an indication of the nature of the object.

Preferred embodiments of this aspect of the invention include one or more of the following features.

The x-ray means comprises an x-ray source and a slit collimator that produces a fan beam.

The detector array means include a linear array of evenly spaced discrete detectors, the array being driven in translation relative to the x-ray means and object through at least two and preferably four sample positions for a distance of travel corresponding to the center-to-center distance between adjacent detectors whereby resolution is enhanced by the multiple nature of the samples taken by each detector in each given scan line.

The detector array means in each scan position of the x-ray means moves a distance corresponding to at least twice the center-to-center spacing of the detectors, and normalizing means are provided, responsive to detection of the same pixel by at least two detectors, over the set of detectors, for normalizing the response for the detectors in the array.

The x-ray source and detector array means are translatable in a direction orthogonal to the second direction to produce the movement in the scanning direction.

Alternatively, the x-ray source and detector means are rotatable to produce the movement in the scanning direction, for instance rotation relative to the object in a CT scanner implementation or rotation relative to the source to produce, in a somewhat simplified manner, a scan similar in effect to a linear scan, albeit with some distortion.

In the cases described, when employing this invention with a fan beam, when the detectors move in the plane of the beam, the source, collimator slit and patient or other object are stationary but when the detectors are moved normal to the beam the detectors are moved with and in fixed relation to the source, and collimator slit, relative to the patient or object.

The detector means includes a linear array of detectors, wherein each detector includes a detector aperture through which detection takes place. This aperture can be a fixed dimension or a variable dimension controlled by a movable mask. The movable mask includes a radiation shield that can be moved in and out of the field of the detectors by a motor or solenoid. The detector array is provided with means to move in the direction of the fan at least equal to the center-to-center spacing of detectors in the array. The output of the detectors is typically sampled two to four times during its travel of one center-to-center distance. The translation in the direction in the plane of the beam can be either incremental or continuous, and is accomplished by a stepping motor in cooperation with a toothed belt, a stepping motor in cooperation with a lead screw, or a dc motor used with a position encoder and a toothed belt or lead screw.

Additional features of the preferred embodiments include a linear array of detectors with measurements in each detector used to normalize a neighboring detector in manner that all detectors can be normalized to each other. To achieve this result the linear array of detectors is adapted to translate a distance equal to more than one and preferably two center-to-center detector spacings in the direction perpendicular to the longitudinal scan direction and transverse to the object for every scan line, i.e., every increment of translation in the direction normal to the plane of the beam. Each detector in the array is adapted to produce detected signals which are compared for x-ray absorption value, which is dependant on the gain of the detectors. The x-ray absorption value is normalized for the detectors, using a multiplying factor which is defined as the ratio of the gain of one detector as compared to the gain of a reference detector. The signals produced by the detectors need to be corrected for gain and offset as well. To correct for the offset in each channel, the signals measured when no x-rays are on is recorded and subtracted from signals when x-rays are on. The gain correction is implemented in a more complicated fashion. By causing each pair of adjacent detectors to travel sufficiently to record identical rays through the patient at some stage during the motion of the detectors in the plane of the fan, the measurements of identical rays by the two detectors can be used to normalize the gain between the two detectors. In this manner, detector two is normalized to detector one, detector three to detector two, detector four to detector three, etc. In order to obtain identical rays measured by two adjacent detectors, as maintained above, the distance of travel of the array along the fan must be more than one center-to-center spacing and preferably two full center-to-center spacings. The gains measured can include an average of the detector gains over a longitudinal scan, an average of the gains over a single scan line, to the object, or determining the gain from a slope-intercept graphing method.

Preferred embodiments also include a power supply which generates a low energy x-ray pulse and a high energy pulse and the calibrating means described in the above referred to applications which are hereby incorporated by reference. The power supply includes a stationary anode adapted to use 1 to 3 milliamps of current. The x-ray means includes fan-producing collimator slits, large and small, with one embodiment being 1 mm in width. The detectors are large, high sensitivity detectors including scintillation detectors in cooperation with photomultiplier tubes. There are approximately 30 rectangular detectors in the array.

According to another aspect of the invention, a bone densitometer apparatus for measuring the bone density of a patient having a length and a thickness includes an x-ray tube means and associated power supply which generates and projects at least one x-ray beam in a plane of the patient. Detector means are arranged on the opposite side of the patient to detect x-rays and produce signals corresponding to the amount of x-rays transmitted through the patient. These detector means are translatable in a direction normal to the plane of the beam and in a direction in the plane of the beam and transverse to the patient. Signal processing means are also included which are responsive to signals from the detector means to produce data on the nature of the bone density of the patient.

Preferred embodiments of this aspect include x-ray exposure along the length of the patient, x-ray exposure laterally along the thickness of the patient, and means used to orient the detection means so that they are adapted to expose the x-ray laterally along the thickness of the patient.

According to another aspect of the invention, a method of performing x-ray analysis on an object includes generating at least one x-ray beam in a plane, exposing the object by passing the x-ray beam through it, detecting the x-rays attenuated by the object using detectors, translating the detectors and the beam in unison in a direction normal to the plane of the x-ray beam to perform a scan on the object, translating the detectors in a direction perpendicular to the plane of the beam and transverse to the object, and processing signals from detected x-rays.

According to another aspect of the invention, a method of increasing resolution in x-ray analysis includes scanning an object longitudinally using an x-ray beam in the plane of the object, detecting through x-ray radiation with a linear array of detectors, each detector in the linear array includes a detector dimension over which the detector can determine x-ray absorption value, and translating each detector in increments perpendicular to the scanning direction and transverse to the object, these increments being smaller than the detector dimension.

According to another aspect of the invention, a method of performing normalization in x-ray analysis includes scanning an object longitudinally to the object using an x-ray beam in the plane of the object, detecting through x-ray radiation with a linear array of detectors wherein each detector has a gain and a detector dimension over which the detector can determine x-ray absorption value (dependant on the gain), translating the linear array of detectors in a direction perpendicular to the scanning direction and transverse to the object so that each detector moves a distance of at least two detector dimensions, comparing the gain of each detector with a gain of at least one other detector for x-ray absorption value, and adjusting the gain of each detector by a correction factor.

This invention has the advantage of performing a high resolution scan using a small percentage of high sensitivity detectors, thereby reducing cost. It also has the capability to perform lateral scans across the thickness of the body which is essential to gather necessary information about the curvature of the spine. Additionally, it provides for a normalized result which guarantees higher accuracy.

Other advantages and features will become apparent from the following description of the preferred embodiment and from the claims.

BRIEF DESCRIPTION OF THE DRAWINGS

A more complete understanding of the invention may be obtained from the following detailed description when taken in conjunction with the drawings, in which.

DESCRIPTION OF THE PREFERRED EMBODIMENT

Figure 1:
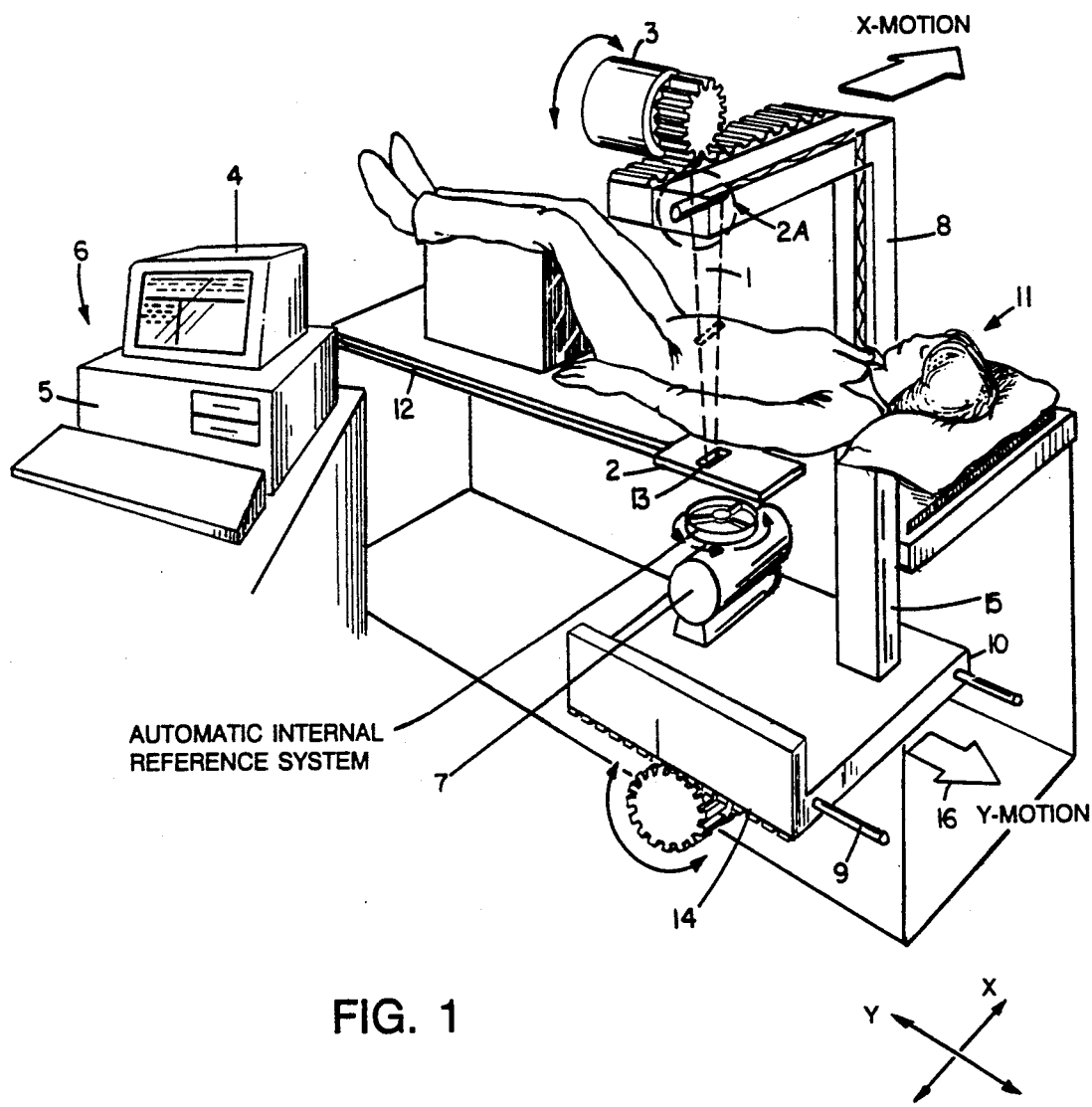
FIG. 1 is a diagrammatic representation of an embodiment of the invention.

An embodiment of a fan beam bone densitometer is depicted in FIG. 1. A patient 11 lies horizontally during scanning on a table 12. X-ray radiation produced by source located beneath the table 12 is transmitted through the patient 11 to an array of detectors, see FIG. 2A, located above the patient.

In more detail, the x-ray source 7 in this embodiment has a stationary anode. Adjacent the source 7 is a slit collimator 13 made of an x-ray opaque material such as lead or tungsten in which one or more selectable slits has been machined. The preferred embodiment includes a 1 mm collimation slit. The x-ray radiation from the source 7 passes through the slit in the collimator 13 and forms a fan shape in space. The width of the beam at the plane of the patient may be such that the width of the patient is completely covered during the scan so that complete skeletal information can be determined, or as often preferred in bone densitometry, the width of the fan may be narrowed depending upon the application, for example to scan a spine only. The x-ray beam not only has width, but also thickness, defined by the width of the slit in the collimator. A scan line is defined by the area of the patient irradiated, i.e. the width and thickness of the x-ray beam over which density data is collected at one point in time. A complete bone densitometry scan measurement therefore consists of a series of adjacent scan lines such that the entire region of interest has been measured.

Opposite the x-ray source 7, approximately thirty detectors 50 are arranged in a linear configuration which spans a part of the width of the patient. The detector array 3 is located on a movable gantry structure 8, and has the capability of moving in two orthogonal directions. In one direction, the detectors move with the gantry 8 and base 10 in fixed relation to the source 7 and collimator slit 13, in a direction perpendicular to the plane of the fan beam which we will refer to as the Y direction, which extends longitudinally along the patient. The detectors also move in the direction along the upper arm of the gantry in the plane of the fan beam, which we will refer to as the X direction, lying transversly across the patient.

To perform a scan, as stated previously, a series of transverse scan lines of data must be acquired. To do this, the x-ray source and the detectors are moved in fixed relation to one another in the Y direction along the patient by moving the gantry 8 and base 10. This motion in the Y direction is responsible for moving the array 3 and source 7 to the next successive scan line during the performance of a complete scan.

This motion can constitute incremental steps or continuous motion. A drive mechanism 14 accomplishes this. For relatively large systems, a toothed belt in cooperation with a stepping motor is utilized to move the gantry 7 and base 10, whereas for relatively small systems, a lead screw is used in cooperation with a stepping motor or position encoder. If continuous motion is utilized, the position of the detector array at any time can be determined by counting the steps in a stepping motor.

As depicted in FIG. 1, the patient is scanned such that x-ray radiation impinges on the back of the patient and exits through the front of the patient (i.e the chest). With this system, it is also possible to scan the patient such that x-ray radiation impinges on one side of the patient (i.e. the shoulder) and exits from the other side. For this type of scan, a mechanism is provided (but not shown) which shifts the position of the gantry structure 8 including the detector array 3 and the x-ray source 7 ninety degrees about the longitudinal axis of the patient. This type of lateral scanning is beneficial because it allows the physician to gather additional information relating to the spinal cord, such as analysis of the isolated vertebral body. In this example, the radiation travels through a thicker section of the object and less radiation is available to strike the detectors. Therefore, it is even more important to utilize highly sensitive detectors such as those described above.

Figure 1C:
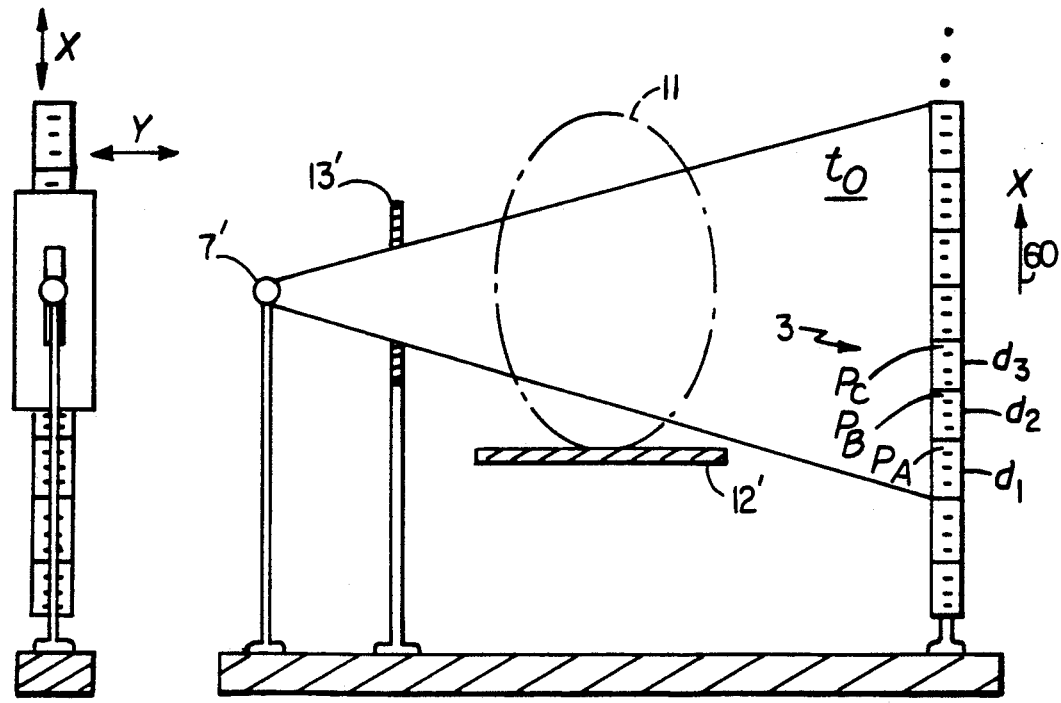
FIG. 1a is a diagrammatic sideview, FIG. 1b an endview and FIG. 1c a topview of an apparatus for performing a lateral scan.
Figure 1C:
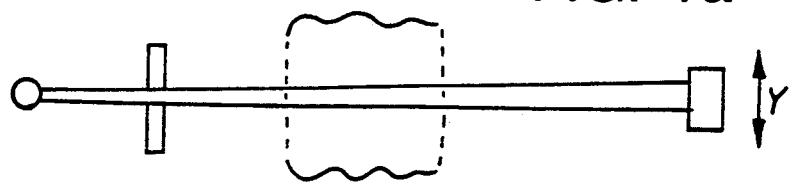

The lateral scan approach is illustrated in diagrammatic FIGS. 1a, 1b and 1c.

Additionally, the detector array 3 is moved in the X direction relative to the x-ray source and slit collimator by a stepping motor 15. This motion is shown diagrammatically for the lateral scan case during a single scan line by the series of positions of FIGS. 3 and 6, subfigures (1) through (8), for the case where the detector array moves over the range of two center-to-center spacings. The important purpose of this x-motion will be described in detail shortly.

In another embodiment of the invention for achieving the necessary motion table 11 is moved in the Y direction rather than moving the base, gantry, x-ray source and detector array. The movement of the table passes the patient through the stationary fan beam to perform the scanning. The table can also be translated in this motion by a stepping motor.

The signals produced by the detectors at successive scan lines are digitized by an analog to digital (A/D) converter in computer 6 and stored on disk. The computer 6 processes the signals from the A/D into density respresentations and images. To form the images from the density data, the computer 6 transforms the digitized density information to a plurality of areas of varying light intensity, displaying this data as picture elements or pixels of a visual image on a video display 4. The video display is capable of displaying both density data and images for viewing by the physician or medical technician.

Figure 2:
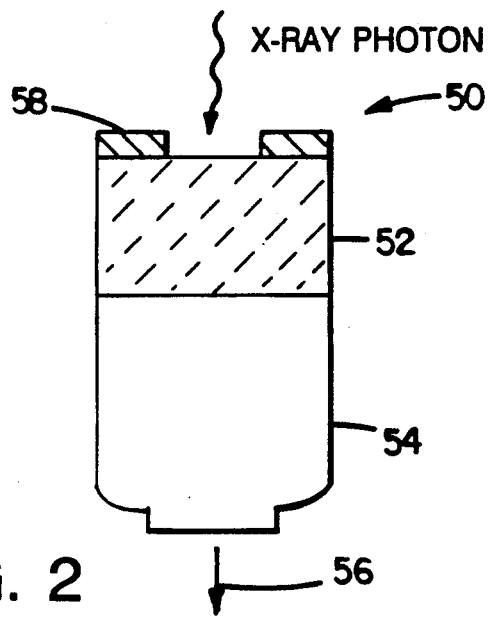
FIG. 2 is a diagrammatic illustration of an x-ray detector of the preferred embodiment.

In more detail, FIG. 2 illustrates an embodiment of a type of detector which can be utilized in this system. The detector 50 includes a scintillation crystal 52 which produces light when struck by the x-ray radiation emitted by the x-ray source 7. The light produced by the crystal 52 is related to the intensity of the x-ray radiation striking it. Adjacent to the scintillation crystal 52 is a photomultiplier tube 54 which amplifies the light produced by the scintillation crystal 52, and generates an electrical signal related to the amount of light produced by the crystal 52. The combination scintillation crystal 52 and photomultiplier tube 54 acts as a highly sensitive x-ray detection device, desirable because of the low level of radiation to which the patient is exposed, especially during a lateral scan. Other detectors such as photodiodes generally are more difficult to use to detect these low levels of radiation. In one embodiment of a bone densitometer, x-ray photons enter the scintillation crystal 52 through an aperture mask 58 which concentrates the photons on one spot on the crystal 52.

Figure 2A:
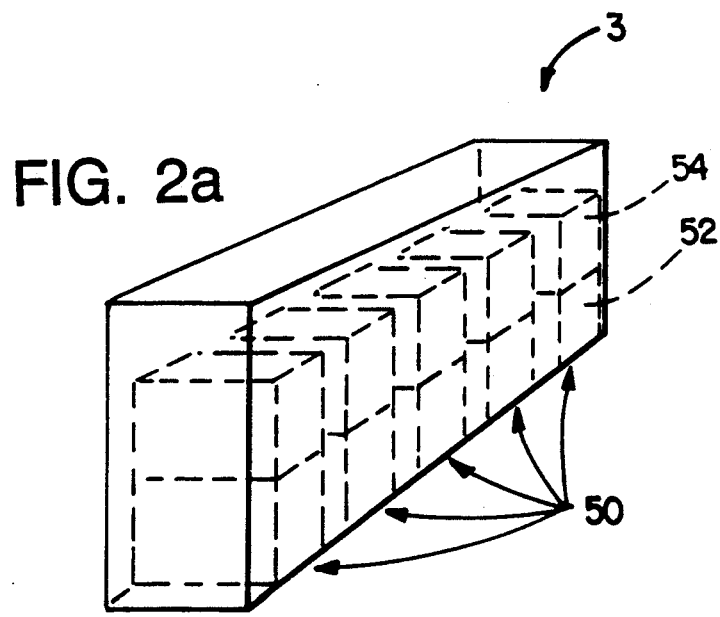
FIG. 2A is a diagrammatic illustration of an x-ray detector array comprising the detectors of FIG. 2.

Referring to FIG. 2A, a series of detectors 50 are arranged in the linear array 3 of approximately twenty to thirty detectors. Each detector 50 generates a signal which provides an indication of the density of bone at the location of the detector within one scan line. As described above, the detectors utilized are highly sensitive. However, these highly sensitive detectors may be too big to supply the resolution sometimes required for certain applications. The invention solves this problem.

In one embodiment, adjacent and relatively small photomultiplier detectors, or, large detectors having masks that make their effective sensitive area small, are positioned such that there is a 0.5" distance from the center of one detector to the center of another detector, i.e. center-to-center spacing. The relatively large spacing reduces the number of detectors required to cover the desired width of the patient scanned and thereby reduces the cost of the detector array. Each detector 50 generates a signal which provides an indication of the density of bone at the location of the detector within one scan line.

Figures 1, 3:
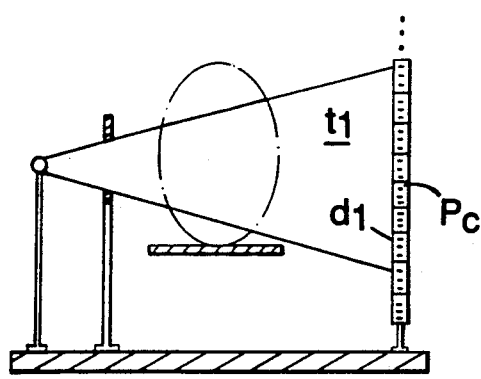
FIG. 3, positions (1) to (3), together with FIG. 1a is a schematic representation of sampling in a single scan pattern as performed in accordance with the invention.
Figures 2, 3:
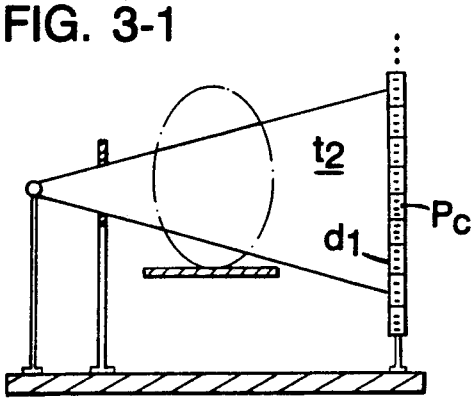
Figure 3:
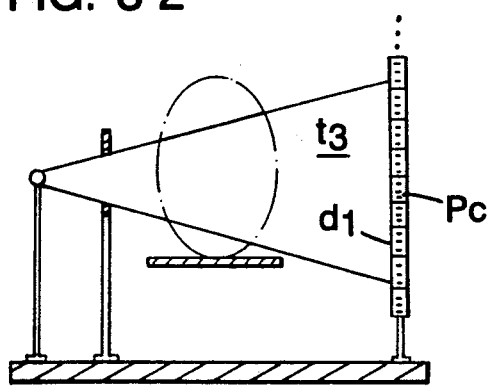

To achieve desired resolution without increasing the number of detectors, the entire detector array is moved along the direction of the scan a distance equal to at least one center-to-center spacing and preferably two. FIG. 3 is a schematic representation of how the detector array 3 is incrementally moved across the patient to increase resolution (only a few detectors are denoted, and each detector is provided with a number of marks by which the successive sampling positions can be understood). An integral number of samples is taken as the array moves for instance one center-to-center spacing. In this embodiment each detector d is sampled at four evenly spaced increments of approximately 0.125" each for each center-to-center distance of travel. This generates signals which are somewhat comparable to a system with four times the number of detectors, thereby increasing the resolution of the system significantly.

In more detail, the motion of the detectors is as follows, referring also to the schematic of FIG. 3. There are (n) detectors 50 denoted (d) in the array utilized to detect the level of x-ray radiation which passes through the body and thereby, to determine the bone density of the patient. Each detector, $d_n$, begins in a home position at time $t_o$ such that the detector aperture is positioned at $d_n{}^{t_o}$, see also FIG. 1a.

In the embodiment, the detectors are spaced such that the effective detector aperture is one-fourth of the center-to-center spacing between detectors. By moving the detector array in the X direction and taking multiple samples per center-to-center detector spacing, measurements then cover all of the space across the patient's scan field. This x-ray image comprises various pixels derived from information taken from every detector in the array at increments small compared to the detector spacing.

Figures 3, 4:
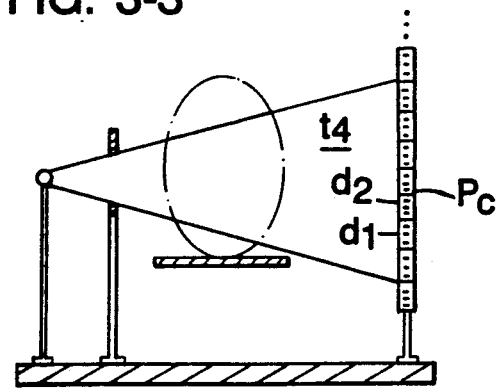
FIG. 4 is a schematic representation of multiple scans as performed in accordance with the invention.

To illustrate this, the detector array and source are positioned in the first scan location, see FIG. 1a, and a sample is taken. Each detector is moved in the X direction (as depicted by arrow 60) and at the next position $d_n{}^{t_1}$ at time $t_1$, a sample is taken. Following that, the detector array is moved to position $d_n{}^{t_2}$, a sample is taken, and similarly to $d_n{}^{t_3}$ to complete four incremental samples of the detector signals in one scan line. This creates an output equivalent to that of a detector array having four times the number of detectors (i.e. an array including 30 detectors will have the resolution of an array having 120 detectors) and therefore, increases the resolution of the system by a factor of four. Following this motion in the X direction, the detector array, source and slit can be translated in fixed relationship to one another, one increment in the Y direction to prepare for another scan line. (In fact, in the embodiment of FIGS. 1a–1c, for purposes elsewhere explained, before advancing to another scan line four more incremental samplings are taken). The detectors are again translated and are sampled at four points in the plane of the fan beam. This motion is in the negative X direction, thus restoring the detectors to their original position. These steps move the detectors from $d_n{}^{t_4}$ to $d_n{}^{t_5}$ and $d_n{}^{t_6}$ and finally to $d_n{}^{t_7}$. FIG. 4 illustrates the proper scanning motion of the detectors in the X direction (as depicted by arrow 65) and the Y direction (as depicted by arrow 70) in such an embodiment. The scanning continues in this back and forth X motion and forward Y motion until a complete scan has been performed. Of course, an alternate embodiment can include scanning in the plane of the fan beam in only one direction, instead of back and forth.

Figure 5A:
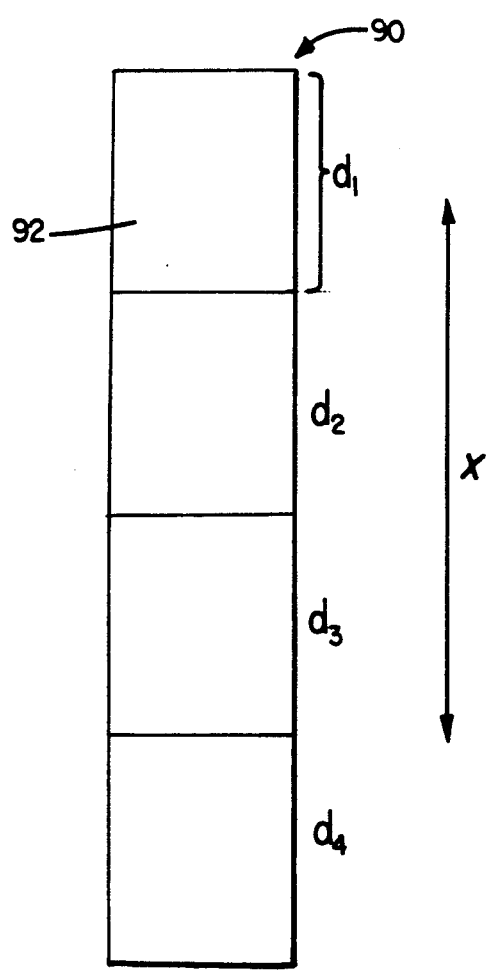
FIG. 5A is a diagrammatic illustration of another embodiment of a detector array.
Figure 5B:
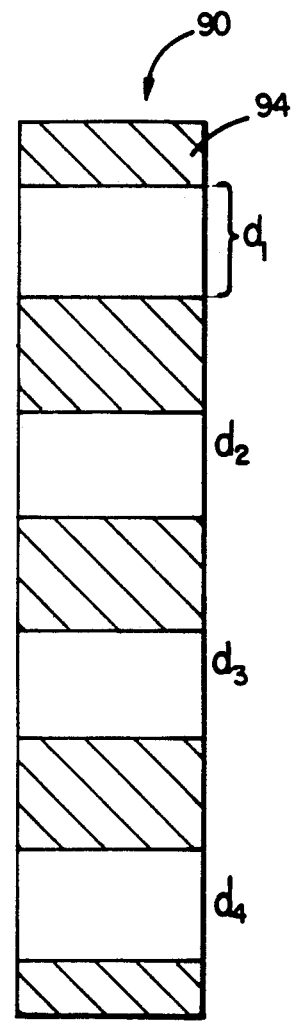
FIG. 5B is a diagrammatic illustration of the detector array of FIG. 5A with a mask.
Figure 7:
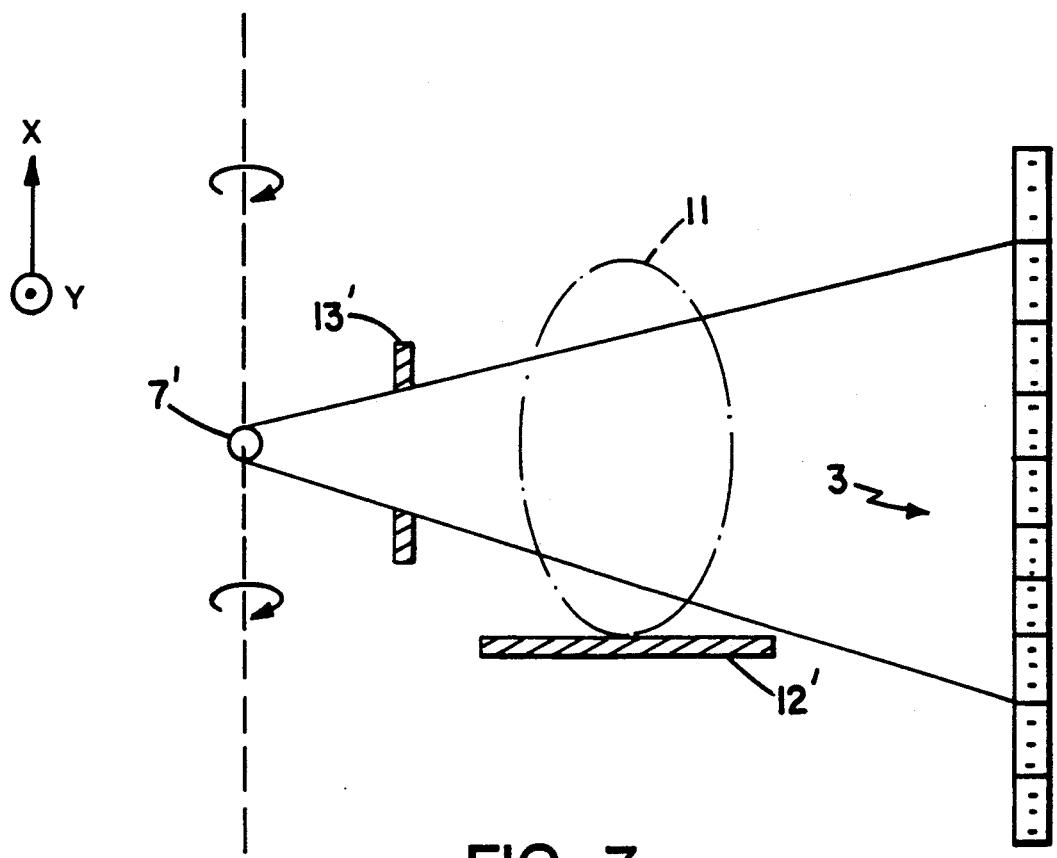

An alternate embodiment of the system described above includes utilizing detectors that are larger than the increment of advance between sampling. Larger detectors are typically easier to mount in array form. Referring now to FIGS. 5A and 5B, a method of varying the effective detector size is disclosed. A detector array including larger detectors will result in a scan having a better signal to noise ratio, whereas a detector array having smaller effective detectors with spacings between adjacent detectors will result in improved resolution using the X-motion scanning described above, at the expense of signal to noise ratio.

FIG. 5A illustrates a linear detector array 90 including relatively large detectors 92, i.e. each detector is approximately 0.5" on a side, which are arranged such that adjacent detectors abut one another. This detector array is sampled four times during the time the array moves one center-to-center distance. There is overlap between detectors during these samples which reduces the resolution, however, even with the overlap the resolution is improved over a system where no X direction movement of the detection is employed, while the larger detector area greatly increases the signal to noise ratio. This feature is very helpful during the side-to-side or lateral scans described earlier because the signal is reduced a significant amount as the x-ray travels through the thickness of the body.

FIG. 5B illustrates the same detector array 90 as shown in FIG. 5A with a lead shield or mask 94 placed over the detector array. This mask blocks out the radiation from the portions of the array that it covers and therefore effectively creates a detector array having detectors with relatively smaller dimensions than those of FIG. 5A. The mask 94 is moved into and out of position on the detector array through the use of a solenoid. The mask when moved into position is effectively attached to and moves with the detector array during both the X and Y scan direction. This array reacts similarly to the detector array described with reference to FIG. 2A. Again, the detector array is sampled in the X-direction in smaller increments than the effective detector dimension to increase resolution. This arrangement has a poorer signal-to-noise ratio than the unmasked arrangement of FIG. 5A, but has improved resolution over that of FIG. 5A arrangement. The arrangement is useful for tasks requiring high resolution, such as obtaining high quality images of the bones.

In many instances, the detectors vary in their gain and therefore will not produce the same signals when exposed to the same x-ray radiation intensity. Therefore, one detector may create an output signal which is higher or lower than the output of another detector. The technique of the invention can be used for normalizing the detectors to produce consistent results.

Figures 5, 6:
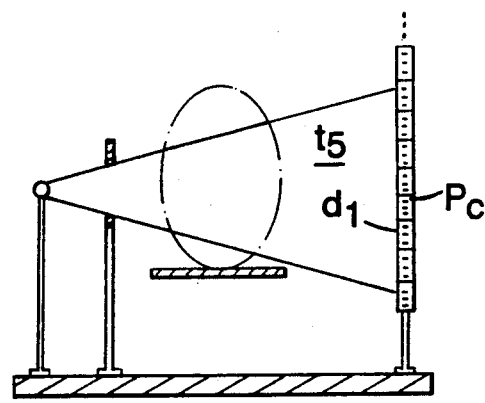
FIG. 6 positions (5) to (8) together with FIG. 3 is a schematic representation of sampling in a single scan line during normalization.
Figure 6:
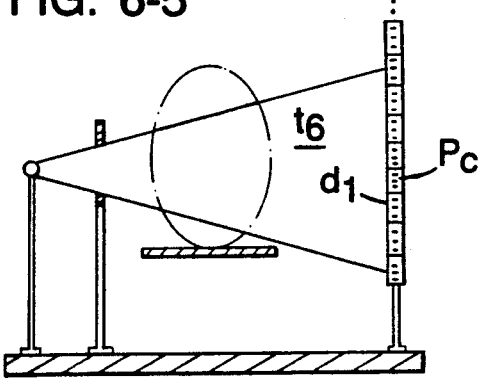

The complete set of positions of FIGS. 1a, 3 and 6 and FIG. 6 illustrate such a normalization process. As the detector system scans the patient (as represented by arrow 60) the radiation in the area corresponding to each pixel is detected by two distinct, adjacent detectors. These two separate signals are "normalized" to a single standard value, which means that the gain of each detector is adjusted to equal the gain of a given detector. Additionally, an offset value is determined for each detector and must be adjusted accordingly. The offset is defined as a residual or dark current in the detector that exists when the detector is not being exposed to x-rays. The offset value is determined for each detector before the x-ray source is powered (i.e. before the scan is taken), and the offset value is subtracted from each measurement taken before the normalization.

Each detector is normalized by comparing the output signal of that detector with an output signal of another detector utilized to measure the identical location on the patient's body. Effectively the gain of detector number one $d_1$, is fixed as a reference. By comparing the measurements in detector $d_2$ that correspond to the same pixels as detected by $d_1$, the gain of detector $d_2$ is normalized to detector $d_1$; then by comparing the measurements in detector $d_3$ that correspond to the same pixels as detected by $d_2$, the gain of detector $d_3$ is normalized to the gain of detector $d_2$ and so on, so that all detectors are in effect normalized to detector $d_1$.

For example, pixel C, a representative point of the body being scanned, in FIGS. 1a, 3 and 6 can be measured during the scan by three detectors $d_1$, $d_2$, and $d_3$ during the course of the detector array translation at corresponding times $t_0$, $t_4$, and $t_8$, respectively. As an example, let detector $d_1$ be used as the reference and the measured value for detector $d_2$ is then scaled by a multiplication factor so that the result equals the measured result at detector $d_1$.

In an actual system, rather than use a single pixel for comparison of two detectors, all pixels scanned by the same set of detectors in a single scan line or over the entire X, Y scan can be used to calculate an average correction factor which is then used for the respective detector for all measurements made in the scan. The average gain measured over the entire scan for detector $d_2$ can thus be normalized to the average gain measured over the entire body scan for a chosen reference detector such as $d_1$, and likewise the average gain of detector $d_3$ measured over the entire scan can be normalized to the average gain for detector $d_2$ and so on. Such an average can be utilized in order to reduce the error in the correction factor. Another method of normalization would be to average the detector gains over each scan line in the X-direction and adjust the gains after each successive scan line is taken.

Normalization actually does not occur in real time, but occurs after all the scans have been completed and the data is input into the computer. A computer manipulation occurs which normalizes each detector over all of the pixels measured by that detector. For example, pixel B is detected by detectors $d_1$ and $d_2$. Therefore, once detector $d_2$ has been normalized to detector $d_1$ for the entire scan, the gain of detector $d_2$ will be adjusted to properly represent all pixels. Of course, the offset value has already been subtracted from the gain measurement.

A graphical normalization technique operative on the signals of neighboring detectors, can be implemented by computer in an alternative embodiment. In such an embodiment, the intercept would represent the offset correction and the slope of the curve would represent, the gain correction factor.

Figures 6, 7:
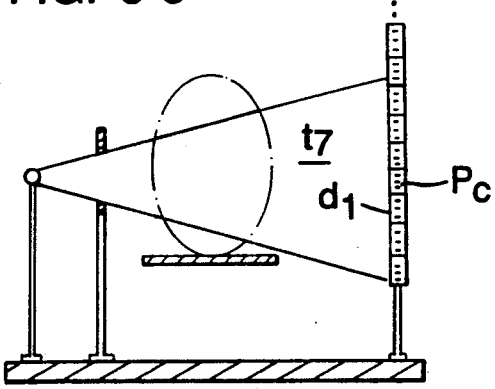
FIG. 7 is a schematic representation of source and detector array rotated together to produce scanning.
Figures 6, 7, 8:
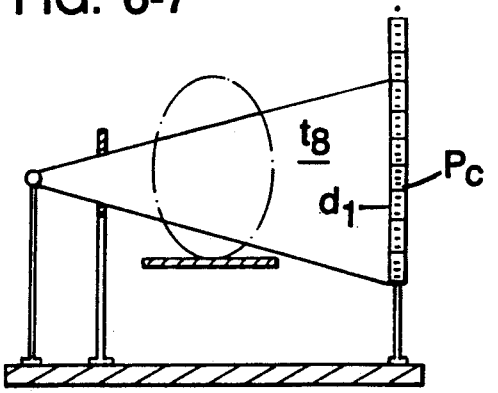
Figure 4:
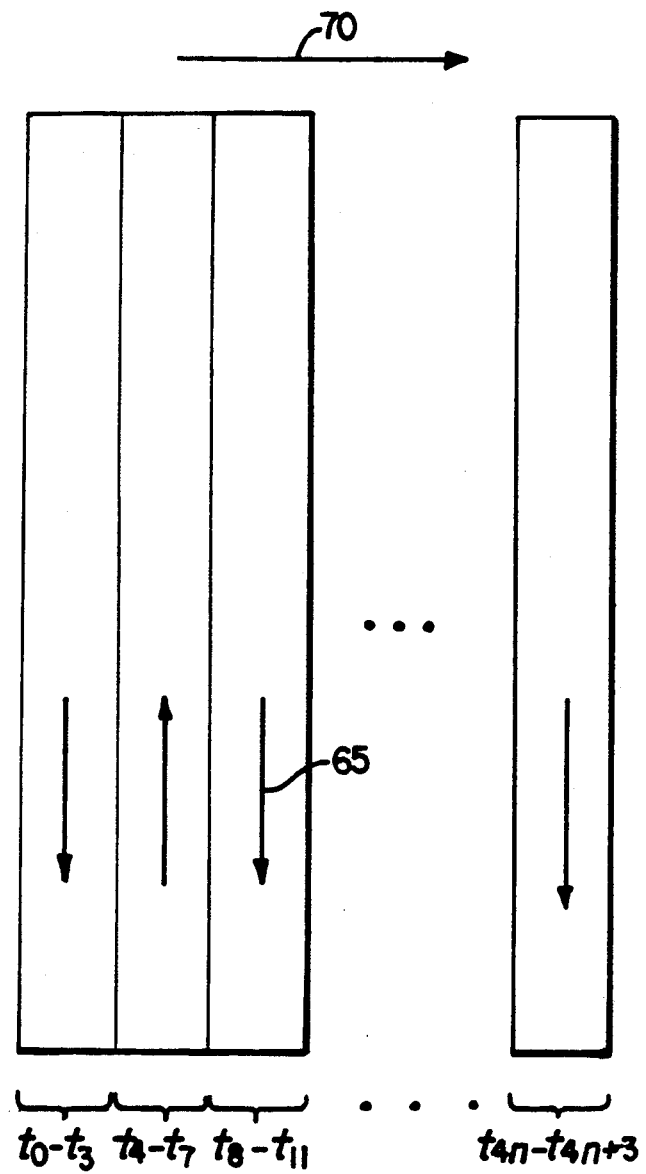

While the scanning motion of the x-ray source, slit collimator and detector array has been illustrated as translation in the y coordinate, other scanning motions are possible. For instance, as shown in FIG. 7, the assembly could be rotated about a line in the plane of the fan beam passing through the x-ray source as center, to approximate translation in the Y direction, in a mechanical movement that is simpler to implement. In the case of a CT scanner embodiment, the assembly can be rotated about the patient.

This disclosure has described a fan beam system for a bone densitometer, but this same system could be applied to other types of x-ray scanners such as cat scanners and baggage inspection systems as well.

Other embodiments of the invention are within the following claims.

What is claimed is:

1. A method of performing normalization in x-ray analysis comprising
   scanning an object utilizing an x-ray beam in a plane,
   detecting through x-ray radiation with a linear array of detectors,
   translating said linear array of detectors in the plane of the beam so that each detector in said linear array of detectors moves a distance of at least two detector dimensions, and sampling the signal of said detectors repeatedly in the manner that each detector detects x-rays at the same pixel as a neighboring detector,
   comparing said gain of each detector with a gain of said neighboring detector for said same pixel, and
   adjusting said gain of each detector by a correction factor dependent upon said comparison.

2. The method of claim 1 further comprising determining said correction factor as the difference between said gain of one detector and the gain of at least one other detector, said one detector being used as a standard, and the correction factor further comprising an offset value.

3. The method of claim 2 further comprising averaging gains measured for said one detector during a longitudinal scan, and comparing said average to an average of gains measured for at least one other detector during said longitudinal scan.

4. The method of claim 1 further comprising averaging gains measured for said one detector during a scan perpendicular to said scanning direction and transverse to the object, and comparing said average to an average of gains measured for at least one other detector during a scan perpendicular to said scanning direction and transverse to the object.

5. An x-ray analysis apparatus comprising an x-ray source means which generates and projects at least one x-ray beam of fan shape in a plane transverse to a desired direction of scan of an object, detector array means arranged on the opposite side of the object to detect x-rays to produce signals corresponding to the amount of x-rays transmitted through the object, said detector array means comprising a plurality of detector elements having a continually exposed sensitive region of predetermined dimension, said detector array means, together with and in fixed relation to said x-ray source means, being movable relative to the object in a scanning direction normal to the plane of the beam through a multiplicity of scan line positions, and said detector array means at each scan line position of said x-ray source means being movably driven in a set of selected equal increments relative to said x-ray source means and the object in a second direction in the plane of the beam, transverse to the scanning direction, a said increment having a length corresponding to a fraction of said predetermined continually exposed dimension of said sensitive region, means to produce, in correspondence with said set of selected equal increments, multiple samples of the signals from each said detector element of the detector array means at each scan line position of said x-ray source means during said movement of said detector array means in said second, transverse direction, and signal processing means responsive to signals from the detector array means corresponding to said multiple samples to produce an image of the object.

6. The apparatus of claim 5 wherein said plurality of detector elements comprise a single linear array in which said detector elements are evenly spaced from center to center.

7. The apparatus of claim 6 wherein each said detector element in said linear array comprises a photomultiplier tube associated with a scintillation crystal.

8. The apparatus of claim 6 further comprising a mask movable into and out of position in front of said detector elements, said mask constructed to limit the exposed region of each of said detector elements, said apparatus operable to produce an image with and without said mask in position, said mask, when moved in position, being effectively attached to and movable with said linear array of detector elements during both movement in said scanning direction and said incremental movement in said second, transverse direction.

9. The apparatus of claim 6 wherein said detector elements in said linear array are incremented and sampled at equally spaced positions between the center-to-center spacing of said detector elements.

10. The apparatus of claim 5 wherein said x-ray source means comprises an x-ray source and a slit collimator to produce the fan-shaped beam.

11. The apparatus of claim 10 wherein said x-ray source comprises an x-ray tube and a power supply, said power supply being constructed to generate both a low energy and a high energy x-ray pulse during said scan of the object.

12. The apparatus of claim 5 further comprising normalizing means for comparing the signal associated with a particular location on the object as detected by at least one said detector element with the signal associated with the same location on the object as detected by at least one other said detector element and adjusting the response of one of said detector elements on the basis of said comparison.

13. The apparatus of claim 5 further comprising offset adjusting means for compensating for the residual current generated by each said detector element when not being exposed to x-rays.

14. The apparatus of claim 5 wherein said x-ray source means and said detector array means are translatable in a direction orthogonal to said second, transverse direction to produce said movement in said scanning direction.

15. The apparatus of claim 5 wherein said x-ray source means and said detector array means are rotatable together to produce said movement in said scanning direction.

16. The apparatus of claim 15 wherein said rotation is about a line in the plane of the fan beam passing through the x-ray source as center.

17. The apparatus of claim 5 further comprising means orienting said x-ray source means and said detector array means to expose the object to x-rays laterally along the thickness of the object.

18. An x-ray analysis apparatus comprising
an x-ray source means which generates and projects at least one x-ray beam of fan shape in a plane transverse to a desired direction of scan of an object, detector array means arranged on the opposite side of the object to detect x-rays to produce signals corresponding to the amount of x-rays transmitted through the object, said detector array means comprising a plurality of detector elements having a continually exposed sensitive region of predetermined dimension, said detector array means, together with and in fixed relation to said x-ray source means, being movable relative to the object in a scanning direction normal to the plane of the beam through a multiplicity of scan line positions, and said detector array means at each scan line position of said x-ray source means being movably driven in a set of selected equal increments relative to said x-ray source means and the object in a second direction in the plane of the beam, transverse to the scanning direction, the size and spacing of said detector elements and the size and number of said increments of movement causing each detector, at least at one of its positions in each scan line position, to overlie the same location on said object as does an adjacent detector element in at least one of its positions in said scan line position, means to produce, in correspondence with said set of selected equal increments, multiple samples of the signals from each said detector element of the detector array means at each scan line position of said x-ray source means during said movement of said detector array means in said second, transverse direction, and signal processing means responsive to signals from the detector array means corresponding to said multiple samples to produce an image of the object, the apparatus further comprising normalizing means for comparing the signal associated with each pair of adjacent detector elements for a particular location on the object as detected by at least one of said pair of detector elements with the signal associated with the same location on the object as detected by the other of said pair of detector elements and adjusting the response of one of said detector elements of each pair on the basis of said comparison.

19. The apparatus of claim 18 wherein a said increment corresponds to a fraction of the center-to-center distance between adjacent detectors and the number of positions in said set of positions of the detector elements at each scan line is selected to cause the x-ray transmission characteristics of all points of the object along said line to be detected.

20. The apparatus of claim 12, 18, or 19 wherein said normalizing means adjusts the response of each said detector element in a serial-dependent fashion over all said detector elements in said array, to approximately equal the response of a preselected one of said detector elements.

21. The apparatus of claim 20 wherein said normalizing means adjusts the gain of a second detector element in said array by a correction factor, said correction factor comprising the difference between the gain of said second detector element and the gain of a first neighboring detector element used as a reference, said second detector element being used to correct a third detector element in the same manner but using said second detector element as a reference, and so on throughout said array.

22. The apparatus of claim 20 wherein an average gain measured over the entire scan of the object for each said detector element is normalized to an average gain measured over the entire scan of the object for a chosen reference detector element.

23. The apparatus of claim 20 wherein an average gain measured over a scan in said second, transverse direction for each said detector element is normalized to an average gain measured over a scan in said second, transverse direction for a chosen reference detector element.

24. A bone densitometer apparatus for measuring the bone density of a patient comprising
x-ray source means comprising x-ray tube means, associated power supply, and collimator slit which generates and projects at least one x-ray beam in a fan beam shape,
detector array means arranged on the opposite side of the patient to detect x-rays to produce signals corresponding to the amount of x-rays transmitted through the patient,
said detector array means comprising a plurality of detector elements having a continually exposed sensitive region of predetermined dimension,
said detector array means, together with and in fixed relation to said x-ray source means, being translatable in a scanning direction normal to the plane of the beam through a multiplicity of scan line positions, and
said detector array means at each scan line position of said x-ray source means being translatable in a set of selected equal increments in a second direction in the plane of the beam, transverse to said scanning direction, a said increment having a length corresponding to a fraction of said predetermined continually exposed dimension of said sensitive region,
means to produce, in correspondence with said set of selected equal increments, multiple samples of the signals from each said detector element of the detector array means at each scan line position of said x-ray source means during said movement of said detector array means in said second, transverse direction, and
signal processing means responsive to signals from the detector array means corresponding to said multiple samples to produce an image of the bone density of the patient.

25. The apparatus of claim 24 further comprising means orienting said x-ray source means and said detector array means to expose the patient to x-rays laterally along the thickness of the patient.

26. A method of performing x-ray analysis on an object comprising:
generating, from an x-ray source means, at least one x-ray beam of fan shape in a plane;
exposing the object by passing said x-ray fan beam through it;
detecting x-rays attenuated by the object utilizing a detector array means, said detector array means comprising a plurality of detector elements having a continually exposed sensitive region of predetermined dimension;
translating said detectors and said beam together in fixed relation in a scanning direction normal to said plane of said x-ray fan beam through a number of scan line positions to perform a scan on the object;
at each scan line position, translating said detectors, relative to said x-ray source means and the object, in a set of selected equal increments in a direction transverse to said scanning direction, a said increment having a length corresponding to a fraction of said predetermined continually exposed dimension of said sensitive region;
producing, in correspondence with said set of selected equal increments, multiple samples of the signals from each said detector element of the detector array means at each scan line position of said x-ray source means during said movement of said detector array means in said transverse direction; and
producing, by utilizing signal processing means responsive to signals from the detector array means corresponding to said multiple samples, an image of the object.

* * * * *